United States Patent [19]
Dunn

[11] Patent Number: 6,157,699
[45] Date of Patent: Dec. 5, 2000

[54] METHOD AND APPARATUS FOR NON-DESTRUCTIVE DETECTION OF HIDDEN FLAWS

[75] Inventor: William L. Dunn, Durham, N.C.

[73] Assignee: Scannex, Inc., Raleigh, N.C.

[21] Appl. No.: 09/311,442

[22] Filed: May 14, 1999

[51] Int. Cl.[7] .................................................. G01B 15/06
[52] U.S. Cl. .............................................. 378/58; 378/98
[58] Field of Search .......................................... 378/58, 98

[56] References Cited

U.S. PATENT DOCUMENTS

| | | | |
|---|---|---|---|
| 4,870,669 | 9/1989 | Anghaie | 378/87 |
| 5,267,296 | 11/1993 | Albert | 378/113 |
| 5,379,336 | 1/1995 | Kramer et al. | 378/98.8 |
| 5,430,787 | 7/1995 | Norton | 378/87 |
| 5,684,851 | 11/1997 | Kurbatov | 378/87 |

OTHER PUBLICATIONS

"A Limited–scan Backscatter Technique for Detection of Hidden Corrosion" Yacout et al, Appl. Radiat. Isot. vol. #48 10–12 pp. 1313–1320, 1997.

"Towards Quantitative Non–Destructive Evaluation of Aging Aircraft" Achenbach, Springer Series in Computational Mechanics, Germany 1991.

*Primary Examiner*—David V. Bruce
*Attorney, Agent, or Firm*—Olive & Olive, P.A.

[57] ABSTRACT

X- or γ-radiation is utilized during non-destructive examination of a sample, to detect hidden flaws in a test sample by generating a number referred to as a single figure-of-merit. The figure-of-merit is obtained by comparing the set of responses obtained from radiation emanating from a standard sample with a set of responses obtained from radiation emanating from a test sample. The resulting figure-of-merit is then compared with a reference value as an indicator of the presence of a flaw.

12 Claims, 9 Drawing Sheets

| I | Scan position (mm) | R | S | T | F | G | H |
|---|---|---|---|---|---|---|---|
| 1 | 828 | 11670 | 11703 | 11554 | 11670 | 11703 | 11554 |
| 2 | 828.999 | 11581 | 11443 | 11525 | 11581 | 11443 | 11525 |
| 3 | 829.997 | 11715 | 11477 | 11682 | 11715 | 11477 | 11682 |
| 4 | 830.996 | 11599 | 11368 | 11860 | 11599 | 11368 | 11860 |
| 5 | 831.994 | 11332 | 11496 | 11637 | 11332 | 11496 | 11637 |
| 6 | 832.993 | 10314 | 11668 | 11706 | 10314 | 11668 | 11706 |
| 7 | 833.991 | 9738 | 11582 | 11524 | 9738 | 11582 | 11524 |
| 8 | 834.989 | 9706 | 11554 | 11522 | 9706 | 11554 | 11522 |
| 9 | 835.988 | 9870 | 11409 | 11516 | 9870 | 11409 | 11516 |
| 10 | 836.986 | 9591 | 11406 | 11764 | 9591 | 11406 | 11764 |
| 11 | 837.985 | 10064 | 11499 | 11616 | 10064 | 11499 | 11616 |
| 12 | 838.983 | 11196 | 11380 | 11525 | 11196 | 11380 | 11525 |
| 13 | 839.982 | 11347 | 11543 | 11567 | 11347 | 11543 | 11567 |
| 14 | 840.98 | 11828 | 11675 | 11447 | 11828 | 11675 | 11447 |
| 15 | 841.979 | 12256 | 11580 | 11416 | 12256 | 11580 | 11416 |
| 16 | 842.977 | 12336 | 11482 | 11713 | 12336 | 11482 | 11713 |
| 17 | 843.975 | 12143 | 11484 | 11548 | 12143 | 11484 | 11548 |
| 18 | 844.974 | 12292 | 11572 | 11586 | 12292 | 11572 | 11586 |
| 19 | 845.972 | 12751 | 11719 | 11534 | 12751 | 11719 | 11534 |
| 20 | 846.971 | 12544 | 11574 | 11610 | 12544 | 11574 | 11610 |
| 21 | 847.969 | 12768 | 11561 | 11434 | 12768 | 11561 | 11434 |
| 22 | 848.968 | 12603 | 11656 | 11568 | 12603 | 11656 | 11568 |
| 23 | 849.966 | 12818 | 11497 | 11714 | 12818 | 11497 | 11714 |

FIG. 14

| I | S | R | G | F |
|---|---|---|---|---|
| 1 | 9902 | 10131 | 0.998387 | 1.002672 |
| 2 | 9987 | 10190 | 1.006957 | 1.008511 |
| 3 | 9957 | 10127 | 1.003932 | 1.002276 |
| 4 | 10143 | 10327 | 1.022686 | 1.02207 |
| 5 | 9992 | 10307 | 1.007461 | 1.020091 |
| 6 | 9945 | 10186 | 1.002722 | 1.008116 |
| 7 | 9997 | 10240 | 1.007965 | 1.01346 |
| 8 | 9919 | 10307 | 1.000101 | 1.020091 |
| 9 | 9799 | 10240 | 0.988002 | 1.01346 |
| 10 | 9815 | 10349 | 0.989615 | 1.024248 |
| 11 | 9719 | 10355 | 0.979935 | 1.024842 |
| 12 | 9956 | 10388 | 1.003831 | 1.028108 |
| 13 | 9828 | 10277 | 0.990926 | 1.017122 |
| 14 | 9810 | 10221 | 0.989111 | 1.01158 |
| 15 | 10006 | 9920 | 1.008873 | 0.981789 |
| 16 | 9855 | 10099 | 0.993648 | 0.999505 |
| 17 | 9755 | 10016 | 0.983565 | 0.991291 |
| 18 | 9737 | 10025 | 0.98175 | 0.992181 |

FIG. 15

METHOD AND APPARATUS FOR NON-DESTRUCTIVE DETECTION OF HIDDEN FLAWS

FIELD OF THE INVENTION

This invention relates to non-destructive examination of samples for the presence of hidden flaws, and more particularly to the detection of flaws using X- or γ-radiation in a manner that leads to a single number, referred to herein as a "figure-of-merit," whose value indicates the probability that a flaw has been detected in a test sample.

BACKGROUND OF THE INVENTION

Flaws occur in many structures and systems, such as in aircraft, ships, trucks, space vehicles, buildings, bridges, pipes, and tanks. The term "flaw" as used herein refers to the presence of a region of abnormal (or different from what is to be expected) density, composition, or shape within a system and includes but is not limited to the following kinds of conditions: stress cracks, corrosion, pitting and surface wear (i.e., the absence of material at a location), scratches and dents, bent or misshapen members, swelling (whether caused by stress or absorption of fluids), delamination (the local separation of layers by air, moisture, or other material), presence of an extraneous object or material within a system (e.g., an object inadvertently left within a structure or a piece of material entwined in a rivet or bolt), or any deviation from the intended or specified configuration or material composition internal to a system or structure. Usually, a flaw is a local condition such as a crack, a small region of corrosion, or a dent.

It is often desirable to detect whether a structure or system contains flaws, since flaws may eventually lead to system failure. However, inspection for flaws can be difficult, time-consuming, and expensive, especially if these flaws are hidden within the structure or system. It is sometimes possible to use ultrasonic, eddy current, radiographic, tomographic, or other means to detect flaws in test objects, particularly if the flaws are near the surface. However, the accuracy and reliability of these techniques or difficulties with their use limit their acceptance as non-destructive techniques for hidden flaw detection. For instance, ultrasonic measurements are non-local in the sense that the sound waves propagate throughout the system and thus are subject to system interferences. Tomographic and radiographic techniques are typically performed in transmission mode which requires access to multiple sides of the test object. Although backscatter tomography and radiography can be applied, these carry safety and maneuverability implications due to high-intensity radiation sources. In addition, all imaging techniques known in the art (ultrasonic, radiographic, tomographic, etc.) require interpretation of images, which is subjective and qualitative.

U.S. Pat. No. 4,870,669 of Anghaie and Diaz, entitled Gamma Ray Flaw Detection System discloses a gamma-ray flaw detection system and U.S. Pat. No. 5,267,296 of Albert, entitled Method and Apparatus for Digital Control of Scanning X-ray Imaging Systems discloses an X-ray digital imaging system. The '669 patent of Anghaie and Diaz discloses an apparatus that generates a collimated monoenergetic G-ray beam used to examine a test object and infer the presence, location, and size of flaws by processing differential scatter gamma spectra. The method disclosed by the '669 patent, however, simply forms "differential spectra" i.e., the features of the difference between two spectra are used to infer the presence, size, and location of flaws. Subtracting one spectrum from the another forms a differential spectrum. If the two spectra are the same, then the shape of the differential spectrum would be approximately a horizontal line at zero height (with some statistical scatter above and below the value zero). If the spectra differ, the differential spectrum would be a set of discrete data points (or a histogram), some portion of which would be nonzero. The '669 patent further discloses a method of finding the approximate location of the flaw, by making a geometrical inference based on the incident beam, the location of the detector, and the scattering angle. The Anghaie and Diaz method requires that the energy spectrum of the scattered γ-rays be measured. Each data point in an energy spectrum is subject to much larger relative statistical uncertainty than is the total detector response irrespective of γ-ray energy. Thus, one shortcoming of the '669 patent is that the difference of two spectra, each of which is subject to statistical counting uncertainties, is itself subject to relatively larger counting uncertainties. The '669 patent does not disclose a method that accounts for differences that are discernible from these counting uncertainties, making interpretation of results somewhat subjective and uncertain.

The '269 patent of Albert discloses a method relating to the non-destructive detection of flaws hidden in a substrate such as an airplane propeller blade. In particular, the method disclosed in the '269 patent produces images on a display screen that are obtained by digital imaging techniques in a transmission mode. Whereas this has apparent appeal, because an image is formed which can be viewed and on which flaws can sometimes be clearly seen, it suffers from certain significant drawbacks. First, the test sample must be placed between the radiation source and the detectors, which limits practical use of the technique to relatively small samples or requires insertion of detectors inside a system (such as inside an airplane wing). Further, the images must be interpreted in some fashion and the technique can be ambiguous when flaws are not clearly discernible visually. This leads to a need for a trained specialist or to sophisticated pattern-recognition algorithms to interpret the image.

With the foregoing in mind, it is the general object of the invention to provide a method and apparatus adapted to use backscatter of a collimated beam of X- or γ-rays to detect— in a non-destructive fashion—flaws in a substrate that are hidden from direct observation by one or more intervening layers of material.

It is a further object of the invention to provide an apparatus and method, when access to two sides of a small or thin sample is easy to achieve, adapted to transmit X- or γ rays to detect hidden flaws.

It is also an object of the invention to provide an apparatus and non-destructive method of detecting faults that leads to a number, i.e., a figure-of-merit, whose value can be used to indicate the probability of detection of a flaw in a test sample.

It is yet another object of the invention to provide a specific probabilistic method and apparatus adapted to form a figure-of-merit indicative of the probability of a flaw in a test sample whose value incorporates natural statistical uncertainties.

It is another object of the invention to provide a non-destructive method and apparatus for detecting the presence and location of flaw(s) in a test sample having only one side of the sample available for testing.

Another object is to provide a flaw detection method and apparatus, which probes the test sample locally and is thus relatively insensitive to system-wide interferences, and which eliminates the need for formation and interpretation of a visual image of a flaw.

The above and still other objects, features and advantages of the invention will become more apparent upon consideration of the following detailed description of illustrative examples thereof, taken in conjunction with the accompanying drawings.

SUMMARY OF THE INVENTION

In accordance with the invention, X- or γ-radiation is utilized during non-destructive examination of a sample to detect hidden flaws in the sample by generating a single number referred to herein as a figure-of-merit.

The apparatus of the invention uses a collimation head incorporating a collimated source of X- or γ-rays and one or more shielded and/or collimated detectors arranged to "view" a small volume at an appropriate depth in both a standard sample and in a test sample. The apparatus of the invention then obtains for each such sample a selected number N of responses, where N is an integer greater than one, by scanning in discrete steps along the surface of each sample. A processing system, such as a computer or person, instructs the collimation head to take discrete steps along a surface of each sample, obtaining responses from different locations along the sample. In the preferred embodiment of the invention, each step taken laterally along the sample is of a lateral size that is generally less than the lateral size of the volume of the sample viewed at each step.

In the optional response conditioning method of the invention, the responses from both test and standard samples are conditioned to form net and/or normalized responses.

Leo form net responses according to the invention, the data collection system measures or calculates a set of background responses, C, such as the responses obtained when the test sample is not present or when only a cover is present (with no substrate), and subtracts C from the scan responses for both the test sample and the standard sample, also referred to as the template. Use of the response conditioning method may improve the sensitivity of the invention method since, by subtracting background responses, any response changes due to flaws present in the substrate become a larger percentage of the net response values.

To form normalized responses according to the invention, the data collection system obtains constants that normalize the responses obtained from backscatter emanating from the standard and test samples (which may have been obtained under different conditions), to similar conditions. Normalizing by using such constants can account for unwanted variations due to source decay, differences in counting time, or environmental conditions such as temperature, all of which may affect absolute responses.

In a significant discovery arising out of practice of the present invention, a set of responses obtained from a test sample is compared to a set of responses obtained in a similar fashion from a standard sample through a single figure-of-merit, which is referred to herein as the template-matching method of the invention. The present invention recognizes that a certain function Z, sometimes referred to as the chi-square statistic, can be used in the context of non-destructive analysis of flaws in a sample, to obtain a single figure-of-merit, by inputting into the formula for Z the set of responses for both the standard and test samples. If the value of Z obtained is sufficiently near unity, then the method of the present invention evaluates the sample as not containing a flaw. However, if Z exceeds a reference value ζ (i.e., if the test-sample responses differ from the standard-sample responses by more than the statistical uncertainties of the responses), then the method of the invention evaluates the sample as containing a flaw.

Another significant discovery arising out of practice of the invention is referred to herein as the rolling-window method. The rolling-window method is able to detect the presence, by calculating a set of Z figure-of-merit values, of very small flaws and of size that would likely go undetected using the traditional methods of image analysis. The present invention recognizes that the figure-of-merit for all responses N may not differ much from unity, even if a few response points in the test sample differ from response points corresponding to the standard sample. This method of the present invention incorporates the template-matching in a "rolling-window" fashion, where the window width is n consecutive scan points (where n<N, the total number of scan points). This is repeated a number of times, typically up to N−n +1. The first time, the start point, I, is 1 and the end point, M, is n. The process is then repeated, with I "rolling" through the values 2, 3, and so forth up to a maximum of I=N−n +1, and M rolling through n+1, n+2, through a maximum of N. This step allows the comparison between F and G (the test sample and standard sample conditioned responses) to a few (n) points at a time, rather than to all points N in the scan. This can be important because if the conditioned response F from the test sample differs from the conditioned response G from the standard only over a subset of the points, the figure-of-merit value of Z, using the rolling-window method of the invention, will show a larger deviation from unity when n is smaller than N. A more detailed description of the invention is next given.

BRIEF DESCRIPTION OF THE DRAWINGS

FIG. 14 is a table containing measured response data R taken from a sample with an internal flaw; S is the set of responses from a standard sample, and T is a second set of responses from a test sample without a flaw. F, G, and H are conditioned responses obtained by subtracting the constant cover-only background, C=1,895 counts, from R, S, and T.

FIG. 15 is a table of data taken from responses obtained from along a section of an aircraft. S are data corresponding to responses obtained over an unflawed rivet; R are data corresponding to responses obtained near a rivet which had a small (hidden) hole near it. G and F are conditioned responses obtained by dividing S by the normalization constant $S_o=9,918$, and R by the normalization constant $R_o=10,104$.

DETAILED DESCRIPTION OF THE PREFERRED EMBODIMENTS OF THE INVENTION

In the description to follow, the reader is cautioned to recognize that there are several kinds of responses, namely, scan responses, net responses, normalized responses, and background responses and therefore, each such term should be interpreted in the context in which it appears. Also, several kinds of methods are dealt with namely, template-matching method, rolling-window method, limited-scan method, and also response-conditioning method and such method terminology should also be interpreted in the context in which it appears.

Figure 1:
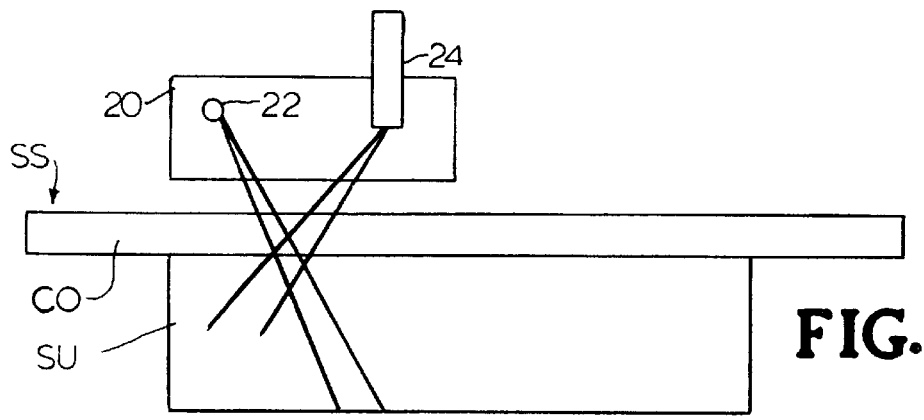
FIG. 1 is a schematic diagram of the major components of the preferred embodiment of the invention apparatus, shown in operational proximity to a standard sample comprised of a cover and a substrate.
Figure 2:
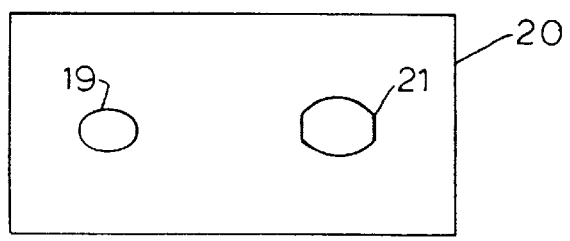
FIG. 2 is a top view of the head of the invention
Figure 3:
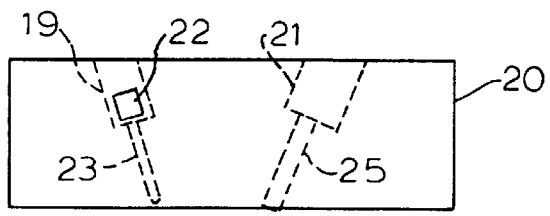
FIG. 3 is a side view of the head of the invention showing the collimators of the invention.
Figure 4:
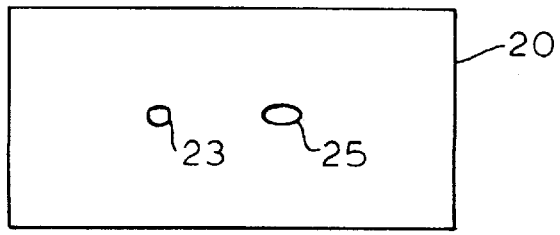
FIG. 4 is a bottom view of the head of the invention showing the exit ends of the collimators.

Referring to FIG. 1 through 4, the apparatus used to implement the method of the present invention includes a head 20 that includes source 22 and detector 24. In the preferred embodiment, head 20 is made of lead or tungsten or some other high-density material that in FIGS. 2,3, and 4 as shown has holes 19, 21, 23 and 25 incorporated therein. Holes 19 and 21 in the head, shown in FIGS. 2 and 3, provide locations to place the source and detector. Other collimation holes 23 and 25, shown in FIGS. 3 and 4, transmit a beam of radiation from the radioisotope source, such as $^{241}$Am or $^{133}$Ba, and allow the radiation detector, such as a NaI(Tl) scintillation detector, to detect radiation emanating from a viewed portion of the sample. In the preferred embodiment, the NaI(Tl) detector is a Model No. IXM.080/2A X-ray detector connected to a Model P14 Scintillator Base, both supplied by Bicron™ of Newbury Ohio. Holes 23 and 25 essentially function as collimators, which direct radiation from the source within a defined beam into a sample, and enable backscatter radiation emanating from the sample to be received by the sensitive part of detector 24. Holes 23 and 25 are typically circular in cross section, although other more sophisticated designs are possible. Each detector 24 is connected to an electronic system (not shown) that provides bias voltage (if needed) and counts the electronic pulses that result from energy deposition in the sensitive part of the detector. Although such components are generally known in the field, a specific embodiment found useful for the present invention is now described in more detail.

Figure 5:
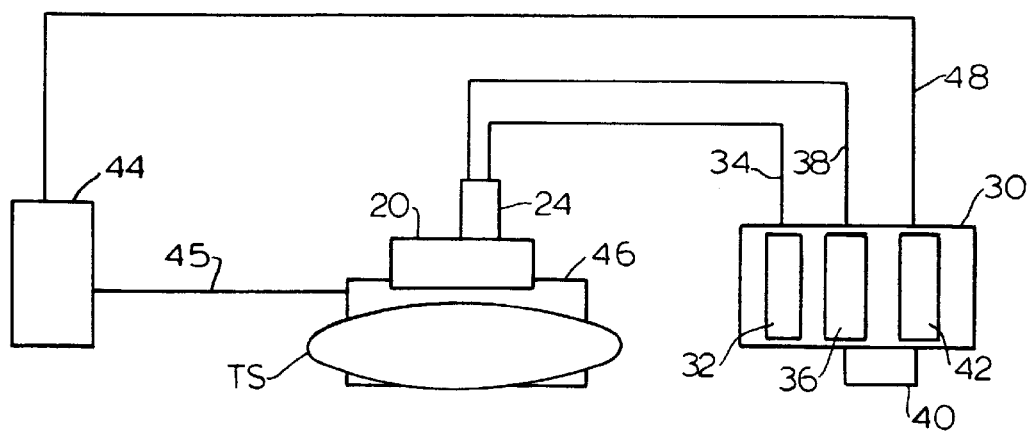
FIG. 5 is a schematic diagram showing the preferred embodiment of the data collection system connected to the detection apparatus of the invention.

Referring to FIG. 5, the electronic system of the invention uses bin 30 within which a high voltage power supply (HVPS) 32 resides and which provides by way of cable 34 a dc voltage to detector 24. Also, bin 30, which is simply an "electronic crate" into which various modular electronic components can be placed, contains a "preamplifier/amplifier/single channel analyzer" (PASCA) 36 to which the output of the detector 24 is connected by coaxial cable 38. Alternatively, a stand-alone preamplifier is used and connected by a cable to a bin-mounted amplifier, which is then connected to a single channel analyzer (not shown). The output of the PASCA 36 is connected by cable 40 to counter/timer 42, also housed in bin 30. Alternatively, the amplifier output can be led to a multichannel analyzer (MCA), either stand-alone or computer-based. The standard components employed in the preferred embodiment, all of which are made by EG&G Ortec™ of Oak Ridge, Tenn., are identified in the following listing:

EG&G Ortec Model 556 High Voltage Supply (32)
EG&G Ortec Model 4890 Preamp-amp SCA (36)
EG&G Ortec Model 994 Dual Counter/Timer (42)
EG&G Ortec Model 401 A Bin (30)

Also shown in FIG. 5 is a stepping motor 46 for moving head 20 relative to the test sample TS in defined steps. Stepping motor 46 moves a carriage along rails (not shown) in fixed steps as small as seven micrometers ($7 \times 10^{-6}$ m). The carriage can be connected to either head 20 (moving it past the sample) or the sample (moving it past the head 20). Other mechanisms for head 20 movement could entail one or more rods along which head 20 is moved by hand between indents, a chain-and gear mechanism that advances the chain as the gear rotates, or a rotating screw along which the scan head advances as the screw is turned.

The final component in this preferred embodiment as shown in FIG. 5 is a personal computer 44 that is connected by cable 45 to stepping motor 46 and by cable 48 to counter/timer 42. Computer 44 contains control software that communicates with and controls stepping motor 46 and counter/timer 42.

Figure 6:
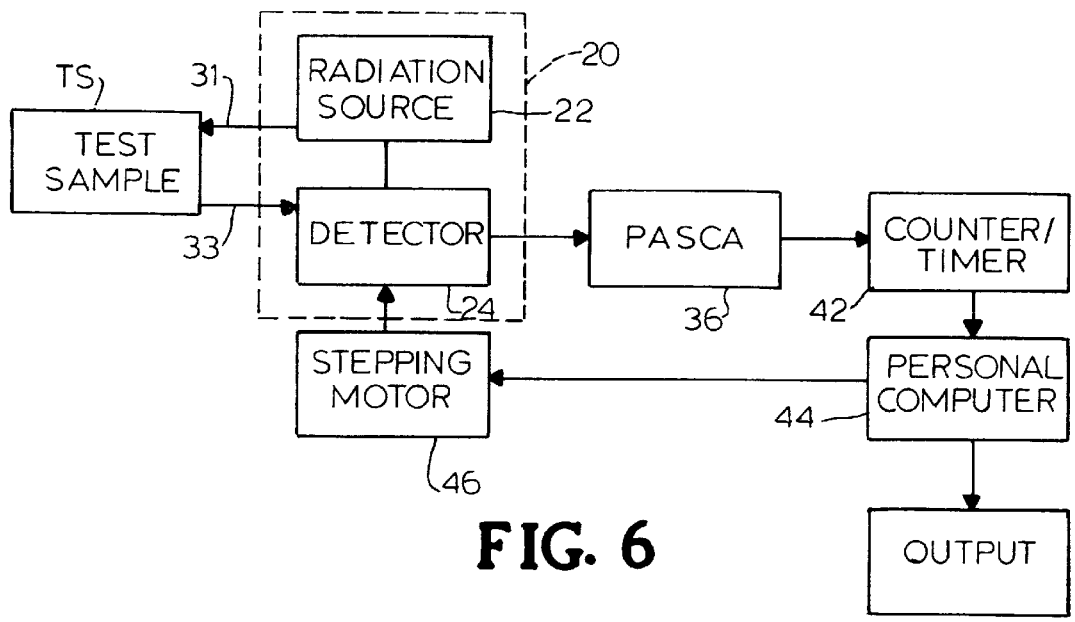
FIG. 6 is a block diagram showing the interconnection and flow of data between the functional elements of the data collection system and detection apparatus of the invention.

FIG. 6 is a block diagram showing the interconnection of the functional elements of the data collection system and detection apparatus of the invention. Computer 44 positions head 20 at a fixed location relative to a test sample TS. Radiation from source 22 is incident on test sample TS as indicated by arrow 31 and backscattered radiation emanating from test sample TS is detected by one or more detectors 24 as indicated by arrow 33. Detector 24 output is transmitted to PASCA 36, where the pulses are preamplified and amplified. Within PASCA 36, those pulses whose amplitudes are greater than a specified lower level (lower pulse height) and smaller than the lower level plus a specified window width (upper pulse height) are passed as output to the counter/timer 42.

Counter/timer 42 receives pulses from PASCA 36 for a count time specified by computer 44 and passes the total counts during that time period to computer 44. This total counts per time period is $R_1$, the response at the first scan position. Computer 44 then sends a signal to stepping motor 46, which moves the head a fixed distance and the procedure is repeated, providing the second scan response, $R_2$ to the computer. The entire procedure then proceeds until N responses have been collected and the scan response profile, R, is stored in computer 44. The data collection system and detection apparatus of the invention performs the same steps described immediately above to collect N corresponding responses from standard sample SS to obtain a scan profile S, which is also stored in computer 44. Computer 44 then processes R and S to form a figure-of-merit Z, or, in the preferred case, a set of plots (one for each rolling-window width, n) of figure-of-merit Z versus I, the rolling-window beginning scan position number as described in more detail below.

Described immediately below is the limited-scan method of the invention for obtaining sets of responses from along the surface of standard and test samples, followed by detailed descriptions of the response-conditioning, template-matching, and rolling-window methods of the invention.

1. Limited-scan method

Referring again to FIGS. 1, 5 and 6, the invention apparatus uses a collimation head 20 incorporating a collimated source 22 of X- or γ-rays (which can be produced by either a radioisotope source or an X-ray machine) and one or more shielded and/or collimated detectors 24 to "view" a small volume at an appropriate depth beneath the cover of a standard sample SS and/or test sample TS (shown in FIGS. 7a through 7d). The apparatus of the invention then obtains a collection of N responses, where N is an integer greater than one, by scanning in discrete steps along the surface of such sample. Also recognized by the invention is the fact that a collection of N responses along standard sample SS or test sample TS can be accomplished by non-scanning means, including utilizing a large head containing a series of sources 22 and detectors 24, such that source 22 and detector 24 pairs are adapted to obtain responses from a plurality of positions at a selected depth along the sample.

From the foregoing description, it is apparent that the invention does not use tomographic techniques, which require multiple independent measures taken through each of many points in a sample in order to reconstruct an image. Instead, head 20 takes discrete steps along surfaces of a sample, obtaining responses from different, but overlapping locations along the sample. In the preferred embodiment of the invention, each step taken laterally along a sample is of a lateral size that is generally less than the lateral size of the volume viewed at each step. In this regard, it is noted that the width of the volume viewed is typically of the order of cm and the step size is typically of the order of mm. The term "lateral size of the volume viewed," indicated by way of example as 27 in FIGS. 7a through 7d, refers to the lateral width of the detector collimator cone at the depth in the sample at which a flaw is suspected.

Figure 7A:
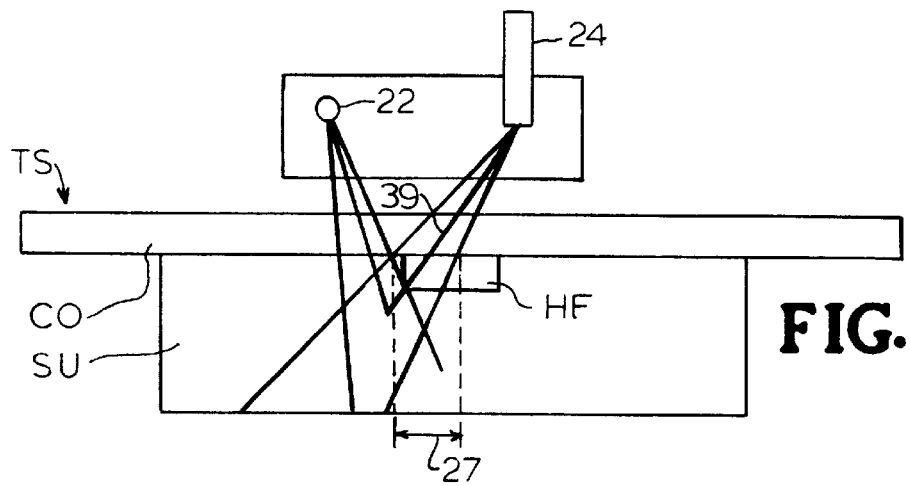
FIG. 7a and FIG. 7b are schematic illustrations of the collimation head of the invention including a source and a detector shown in two positions along the surface of a sample containing a horizontally oriented disk-shaped flaw by way of illustration.
Figure 7B:
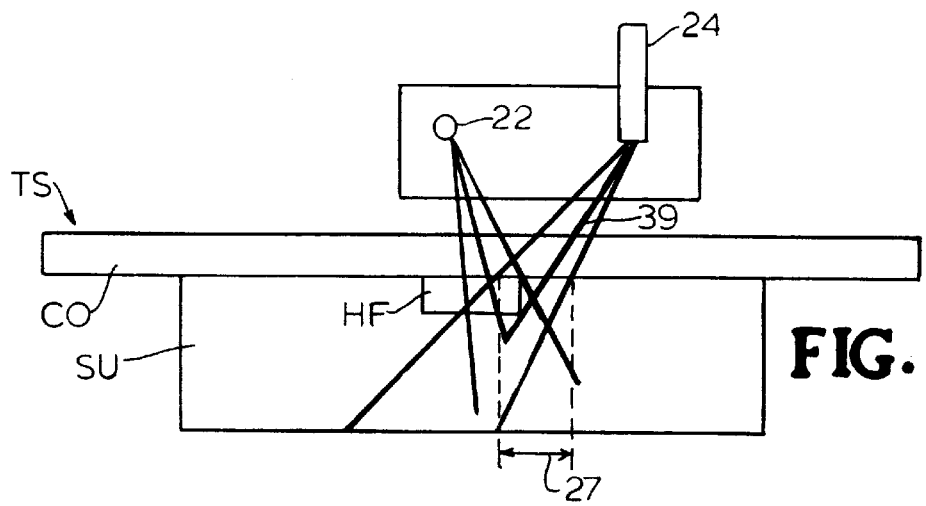
Figure 8B:
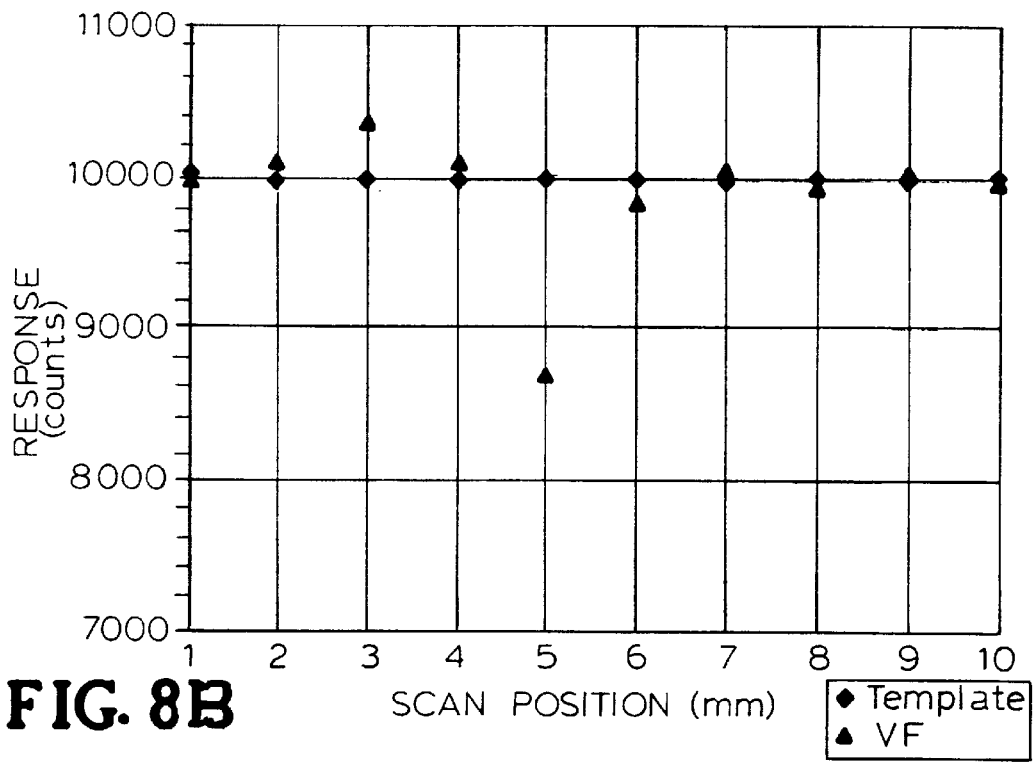
FIGS. 8a and 8b are graphical illustrations of responses obtained from positions of the collimation head of the invention including positions shown in FIGS. 7(a) and 7b, and FIGS. 7c and 7d, respectively.

Referring to FIGS. 7a through 7d, the method of obtaining a set of responses along a test sample TS is illustrated by way of example. FIGS. 7a and 7b by way of example illustrate an idealized horizontally oriented disk-shaped flaw (HF). At the first scan position, shown in FIG. 7a, a portion of the source beam scatters in unflawed material and a portion of the scattered photons encounter the flawed region on their exit to detector 24, as indicated by line 39 which represents a typical photon singly scattering in the sample. The response of detector 24 in this case will differ (corroded areas, for example, are less dense than the surrounding sample) from the response if no flaw were present, due to different (generally lower) attenuation within the disk-shaped flaw HF leading to generally higher response. At a later scan position as shown in FIG. 7b, for example, five scan steps later, some of the source photons will encounter disk-shaped flaw HF before scattering and hence the depths at which they scatter will be affected (generally, such depths will be increased). Thus, the differences in scan positions in reference to the disk-shaped flaw HF lead to differences in the average depth of scatter, and to differences in attenuation of the entering and exiting beams, resulting (when passing through a fault) in differences in the expected detector 24 response. If the overlap region of source 22 and detector 24 collimators and the scan step size are properly chosen, a scan profile of the disk-shaped flaw HF such as shown in FIG. 8a will result, which will differ from the scan profile of the standard sample SS, also referred to herein as the "template" (represented as responses of constant value in FIG. 8a) that is expected for an unflawed standard sample.

Figure 7C:
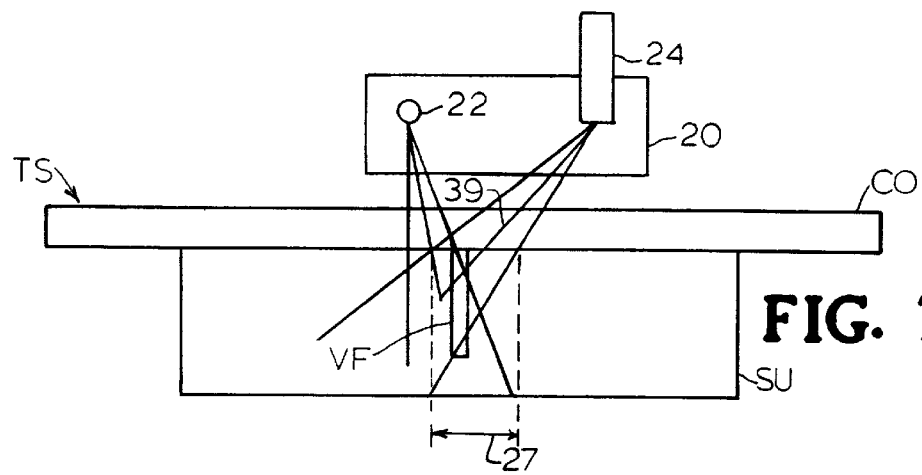
FIG. 7c and FIG. 7d are schematic illustrations of the collimation head of the invention including a source and a detector shown in two positions along the surface of a sample containing a vertically oriented crack-shaped flaw by way of illustration.
Figure 7D:
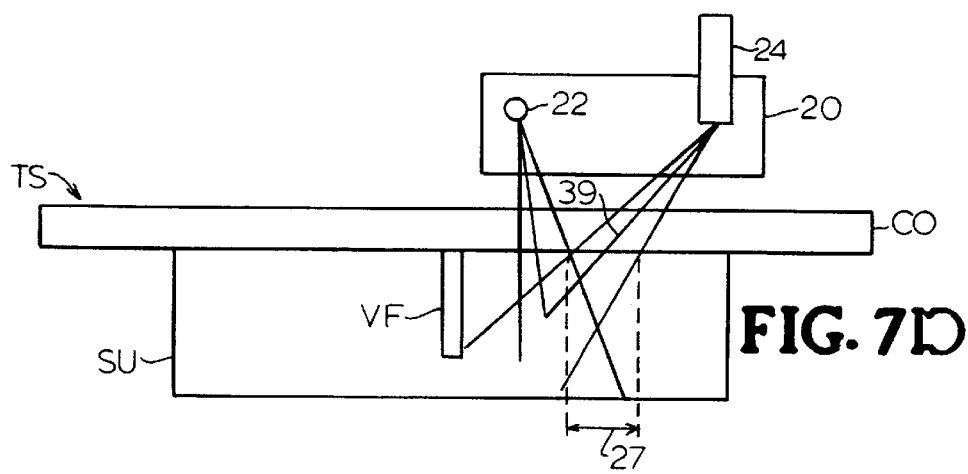
Figure 8A:
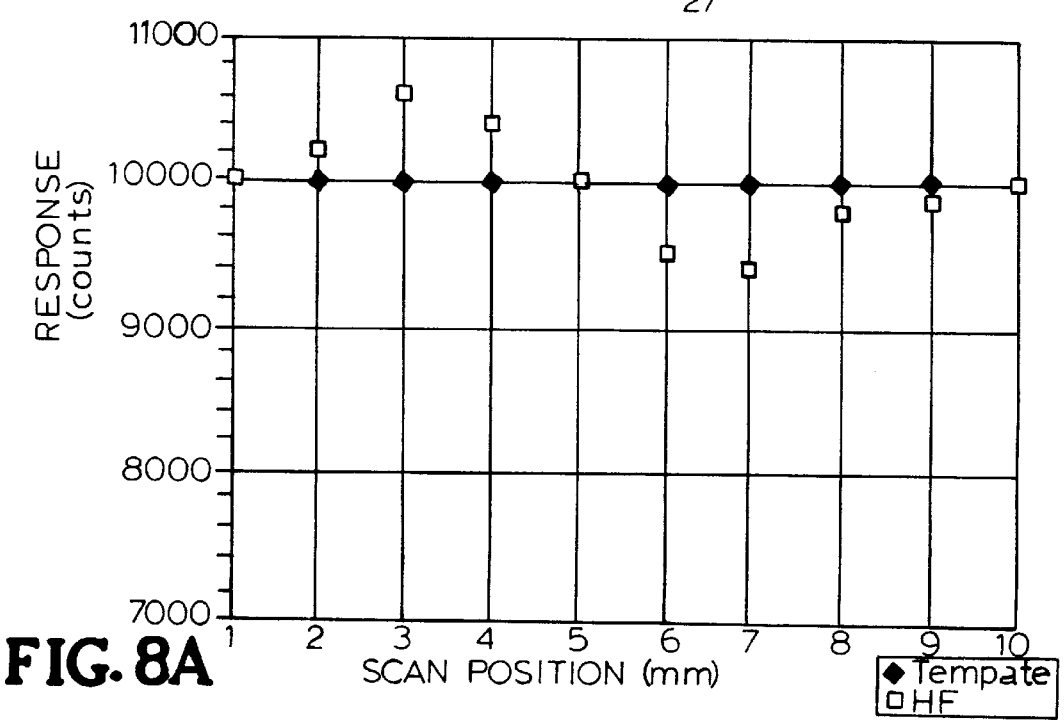

FIGS. 7c and 7d illustrate use of the present invention for detecting a thin vertically oriented flaw (VF), such as a crack. For a vertically oriented flaw VF, the scan profile will be somewhat different than that for scan profile for the disk-shaped flaw HF illustrated by FIGS. 7a and 7b. FIGS. 7c and 7d show an idealized flaw VF with head 20 shown at the same two positions as illustrated by FIGS. 7a and 7b, respectively. At the first scan position the response will be changed (generally increased) due to different (generally lower) attenuation within the vertically oriented flaw VF. However, by the time head 20 is at the position shown in FIG. 7d, no single-scattered photons are transported through flaw VF (although a few multiple scattered photons might be) and the response will be near the no-flaw template level. FIG. 8b shows the unique scan profile I-or the vertically oriented flaw VF shown in FIGS. 7c and 7d.

Although FIG. 1, and FIGS. 7a through 7d show the substrate as a large continuous medium beneath a flat cover CO, the method applies to many other types of samples as well. For instance, the substrate SU could be a structural member (such as a beam, rod, or angle section), a sheet similar in shape to the cover (such as a second aircraft skin), an odd-shaped object (such as a hinge or flange), a part of the cover itself (such as the inner portion of a steel pipe), or any material that is hidden from direct observation by an obscuring surface layer.

The cover CO and substrate SU can be composed of any of a variety of materials, such as metal, plastic, glass, and even fluids. However, for the method to work well, the materials should be relatively uniform or if non-uniform the non-uniformity should be well characterized (e.g., a woven material such as a cloth whose weaving pattern is regular and known). The invention also recognizes that in large structures such as aircraft it is often impractical to examine the sample in a transmission mode and so the invention is primarily concerned with backscattered radiation; however, the method of the invention applies equally well to detector response scan profiles obtained in a transmission mode, where the source and detector are on opposing sides of the sample.

The responses for both the test sample and the standard sample using the limited scan method are generally described as follows:

Let R be the set of N responses for the test sample, viz.

$$R=\{R_k, k=1,2,\cdots N\} \quad \text{(Equation 1)}$$

and S be the set of N responses for a reference or standard sample, viz., $$S=\{S_k, k=1,2,\cdots N\} \quad \text{(Equation 2)}$$

where $R_k$ and $S_k$ are the total detector counts obtained on the test and the standard samples, respectively, at the $k^{th}$ scan position. S is referred to herein as a template.

In the preferred embodiment it is recognized that:

The scan conditions should be as nearly identical as possible for the test sample and the standard sample.

The scan step size can change during the scan as long as it does so in a similar fashion for both the test and the standard samples.

The scans do not have to be linear, although they often will be. For instance, it would be possible to scan part or all the way around the curved surface of an airplane wing section or a pipe or tank.

It is possible, and sometimes preferable, to use more than one detector in order to improve counting statistics or for other reasons. The terms "detector" and "response" are thus used to refer to one or more detectors being used and one or more responses that are obtained for each scan position.

It is not essential that both source and detector be collimated, as in FIG. 1, although it is preferable that both are, in order to improve signal-to-noise ratio; however, the method of the present invention does requires that at least one (source or detector) be collimated.

It is possible, in principle, to use computer simulation to form the template, S, for the standard sample.

2. Response-conditioning method.

The present invention also recognizes the benefit of conditioning the responses, such as by forming net and/or normalized responses. To form net responses, the method of the invention measures or calculates a set of background responses, C, such as the responses obtained when no test sample is present or when only cover CO is present (with no substrate SU), and subtracts C from the scan responses for both the test sample TS and the standard sample SS. This is implemented by the method of the present invention in the following manner. Let C be the set of N background responses, viz.

$$C = \{C_1 C_2, \ldots, C_N\} \quad \text{(Equation 3)}$$

C can be obtained without the substrate SU present (cover-only response) or alternatively with no sample at all (simple background). Then, net responses, F and G are formed by subtracting C from R and S, viz.

$$F = R - C \quad \text{(Equation 4a)}$$

and $$G = S - C. \quad \text{(Equation 4b)}$$

If C is the response with cover CO only (no substrate SU) then the subtraction process removes counts that come through the head 22 or only from cover CO and thus which contain no information about conditions below cover CO. If cover CO and substrate SU are uniform over the scan path, the $C_i$ may be estimated by a single count, C, i.e., $C_i = C$, $i = 1, 2, \ldots, N$, where C is a count obtained at a single position above the cover only. The invention recognizes that this seemingly minor step may improve the sensitivity of the invention method since, by subtracting selected background responses, any response changes due to flaws present in the substrates become a larger percentage of net response values.

Alternatively, or in addition, one can form normalized responses as follows $$F = \frac{R}{R_0} \quad \text{(Equation 5a)}$$

or $$F = \frac{R - C}{R_0} \quad \text{(Equation 5b)}$$

for the test sample TS and $$G = \frac{S}{S_0} \quad \text{(Equation 6a)}$$

or $$G = \frac{S - C}{S_0} \quad \text{(Equation 6b)}$$

for the standard sample SS, where $R_0$ and $S_0$ are constants that normalize F and G to similar conditions. The value of $S_0$ should be obtained at the time that the standard sample SS is determined for a condition that can be duplicated in the field (e.g., a response with no sample or with a solid block for a sample). The value of $R_0$ is then obtained in the field at the time that the scan for the test sample is obtained in a manner similar to that used to obtain $S_0$. Alternatively, the invention recognizes that the values of $S_0$ and $R_0$ could be the counting times, if the scans for the standard and test samples are obtained for different counting times at each scan step. Normalizing by $S_0$ and $R_0$ therefore, can account for variations due to source decay, counting time, or environmental conditions such as temperature that may affect absolute responses. Also recognized is that normalizing by $S_0$ and $R_0$ may improve the sensitivity of the invention method.

Neither the subtraction nor the normalization steps are essential; if neither is applied, consider the formalism of Equations 4–6 with all the $C_i = 0$, and/or with $R_0 = S_0 = 1$, so that:

$$F = R \quad \text{(Equation 7a)}$$

and $$G = S \quad \text{(Equation 7b)}$$

Figure 9:
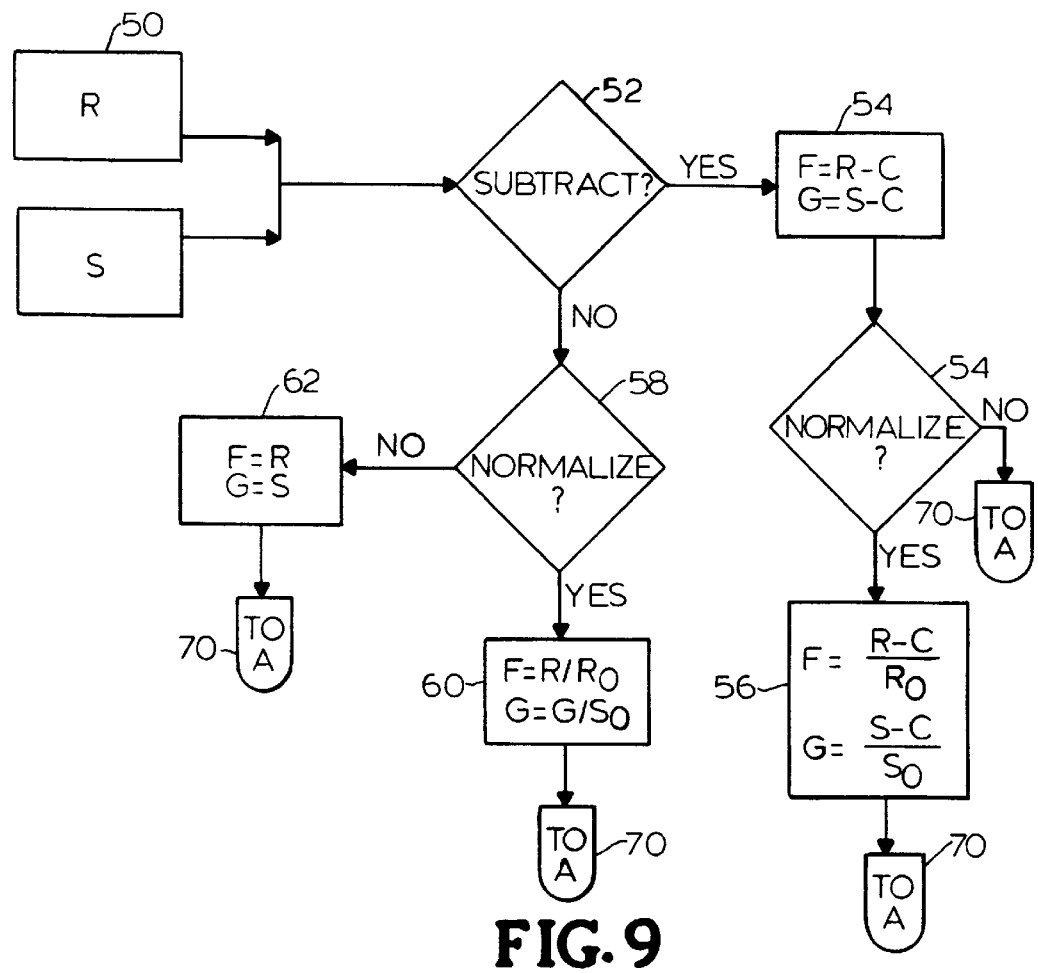
FIG. 9 is an operational flow diagram illustrating the steps of the response-conditioning method of the invention.

FIG. 9 presents a flow chart that schematically describes the steps involved in the response conditioning method of the present invention. Measured responses R and S are first obtained as indicated at 50. If the background response C is to be subtracted as indicated at 52, such as the cover-only response, Equations (4a) and (4b) are performed at 54 as indicated in FIG. 9. If normalization is also desired as indicated at 54, Equations (5b) and (6b) are performed as indicated at 56. If the background response is not subtracted, but normalization is desired as indicated at 58, Equations (5a) and (6a) are implemented as indicated at 60. If neither background subtraction nor normalization is performed, Equations 7(a) and 7(b) are implemented at 62.

3. Template-matching method.

The method of the present invention also compares the set of responses, R, obtained from test sample TS to the set of responses, S, obtained in a similar fashion from the standard sample SS to obtain a single figure-of-merit, in a method of the invention referred to as template-matching. Test sample TS response R is converted to response F and standard sample SS response S is converted to response G in one of the manners described above.

In template-matching, a figure-of-merit is determined by finding $$Z(I, M) = \sum_{i=I}^{M} \frac{[G_i - F_i]^2}{\sigma^2(G_i) + \sigma^2(F_i)} \quad \text{(Equation 8)}$$

where $\sigma(G_i)$ is a measure of the uncertainty in the response $G_i$, $\sigma(F_i)$ is a measure of the uncertainty in $F_i$, and I and M are integers between 1 and N, with M>I; an obvious choice is I=1 and M =N. M is the number of the final scan point and I is the number of the first scan point used to construct the value Z. Typically, if the responses were obtained under similar conditions, the uncertainties are obtained from the responses as follows $$\sigma(F_i) = \sqrt{R_i + C_i} \quad \text{(Equation 9a)}$$

and $$\sigma(G_i) = \sqrt{S_i + C_i} \quad \text{(Equation 9b)}$$

Equations (9a) and (9b) apply whether C is measured or all the $C_i$ are zero.

Alternatively, if the responses are normalized, the uncertainties can be estimated by $$\sigma(F_i) = 1/R_0 \sqrt{\sigma^2(R_{i)+F_i 2\sigma^2)(R_0)}} \quad \text{(Equation 10a)}$$

and $$\sigma(G_i) = 1 R_0 \sqrt{\sigma^2(S_{i)+G_i 2\sigma^2(S_0)}} \quad \text{(Equation 10b)}$$

The function Z is sometimes called the least-squares function or chi-square statistic; its use in comparing two distributions is known (see, Press, et al., *Numerical Recipes in Fortran 77; The Art of Scientific Computing*, Cambridge University Press, 1996). As a statistical procedure, it is often used to test whether a set of measured responses differs statistically from an assumed distribution (such as the Poisson, the Gaussian, the Lorentzian, the Binomial, the Exponential, etc.). If the value of the chi-square statistic is near unity, then the measured responses are assumed to "fit" the assumed distribution; otherwise, they are not.

It is recognized that the least-squares function has been used in radiation counting applications but in a different way from that of the invention. For instance, consider a Gaussian function, $g(\mu,\sigma,E)$, where p and a are parameters (the Gaussian mean value and standard deviation) and E is radiation energy. The process of fitting a Gaussian to a measured detector response energy distribution (often called a spectrum), $P = \{P_k, k=1, 2, \ldots, K\}$ is often performed by minimizing the least-squares function $$L(\mu, \sigma) = \sum_{k=1}^{K} \frac{[g(\mu, \sigma, E_k) - P_k]^2}{s_k^2}$$

where $s_k$ is an estimate of the statistical uncertainty in the measured value of $P_k$ and is usually taken as $$s_k \sqrt{P_k} = 4.$$

Then the values of $\mu$ and $\sigma$ for which L is minimized determine the Gaussian function that best "fits" the data P. Procedures such as this are used, for example, in energy-dispersive X-ray fluorescence analysis, in prompt gamma ray neutron activation analysis, and in X-ray photoelectron spectroscopy (XPS). Typically, in such cases, several Gaussians (or other functions) are fit to a measured spectrum that contains many peaks. The values of $\mu$ identify the characteristic radiation energies that a sample emits; these energies then identify the elemental composition of the sample or, in the case of XPS, the binding energies of the chemical bonds in the sample. Such a procedure is described, for instance, by Dunn and Dunn ("An Asymmetric Model for XPS Analysis, *Surface and Interface Analysis*, Vol. 4, No. 3, pp. 77–88). The present invention, however, differs from using the least-squares function as a tool for fitting a function to data. Rather, the invention method interprets the value of Z as a measure of whether the set of test sample responses and the set of standard sample responses are statistically different; this use of the chi-square statistic in analyzing limited-scan responses has not been reported, as far as applicant is aware.

The value of Z should be close to unity if the response from the test sample, F, is statistically similar to the response from the standard, G. If the responses differ by more than the statistical uncertainties in F and G, the value of Z will be larger than unity. Then, if the value of Z exceeds a selected value $\zeta$, we conclude that there is probably a flaw in the test sample. A typical value to select is $\zeta=1.5$. The value selected determines the sensitivity of the flaw analysis. The higher the value of Z, the more likely it is that a flaw is present. Thus, if $Z>\zeta=2$, one is more certain that a flaw is present. If one wishes to be conservative, one can use a low value, such as $\zeta=1.25$, in which case it is less likely that a flaw will go undetected but more likely that a test sample without a flaw will be identified as possibly having one.

The method of the invention allows a user to decide what probability level to use simply through selecting the value of $\zeta$. Further, the invention allows comparison of responses obtained at different times or under different conditions (temperature, humidity, etc.) through use of the normalization methods implemented by Equations (5) and (6).

4. Rolling-window method.

The invention further recognizes that if there is a flaw at some location in the substrate along the test sample scan, it may affect only a portion of the scan (when the scan head is near the flaw location). The rest of the scan responses should be similar to the scan responses corresponding to the template. The value of Z for all N points (the total number of scan points) may not differ much from unity even if a few response points in the test sample scan differ from the template scan. Recognizing this, the invention includes a method that compares only parts of the test scan and template scan at a time. This method of the invention incorporates as described above the template-matching in a "rolling-window" fashion, where the window width is n consecutive scan points (where $n \leq N$). This is repeated a number of times, typically up to N–n. The first time, the start point, I, is I and M is n. Of course, M is the number of the final scan point that is used to construct the rolling-window value for the function Z, and I is the first scan point that is used to construct the rolling-window value for the function Z. The process is then repeated, with I "rolling" through the values 2, 3, and so forth up to a maximum of I=N–n+1, and M rolling through the values of M=1+n–1, through at most N. This step allows the comparison between F and G to a few (n) points at a time, rather than to all points N in the scan. This can be important because if the conditioned response F from the unknown differs from the conditioned response G from the standard only over a subset of the points, the figure-of-merit value of Z, using the rolling-window method of the present invention, will show a larger deviation from unity when n is smaller than N.

The rolling-window method of the invention also allows n to take on different values. For instance, if N were, say, 20, then template-matching could be performed for N=20, and smaller values n, say n=15, n=10, and n=5. If Z remains below $\zeta$ for all rolling-window comparisons, the sample is unlikely to contain a flaw. If, on the other hand, Z exceeds $\zeta$ for one or more sets of n points, the test sample TS should be suspected of having a flaw such as hidden corrosion or some other density/composition change. It is noted that the set of n points for which Z exceeds $\zeta$ identifies approximately where the flaw is within the test sample.

Figure 10:
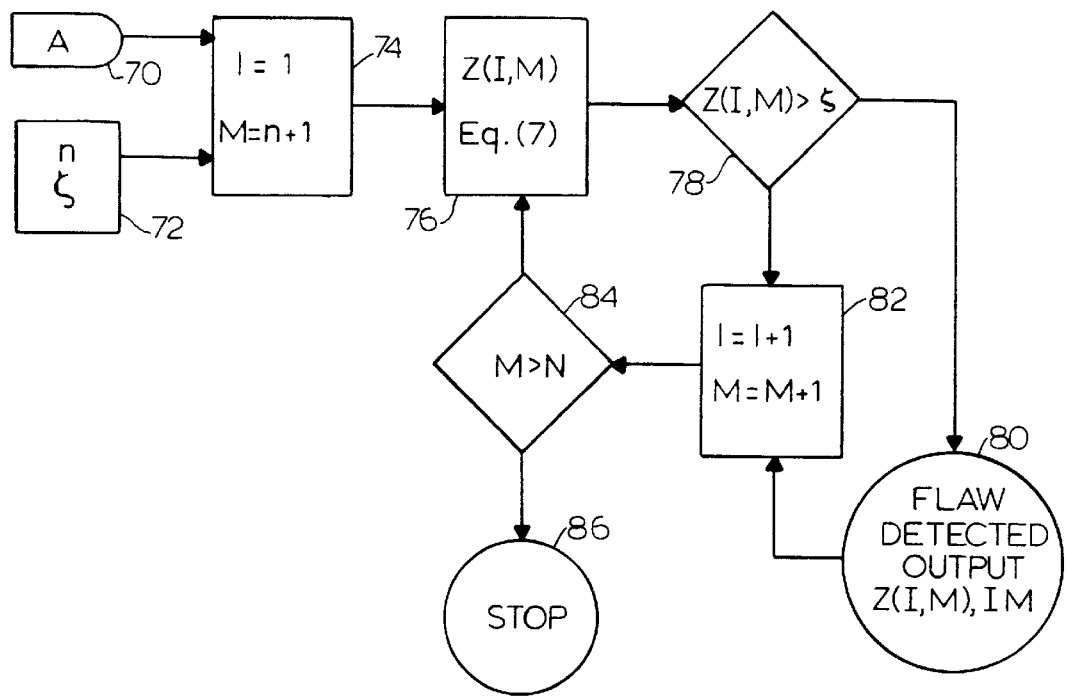
FIG. 10 is an operational flow diagram illustrating the steps of the template-matching and rolling-window methods of the invention.

FIG. 10 shows a flow diagram of an implementation of the rolling-window method of the present invention. The output of the response-conditioning step is the number of scan points, N, the response profiles F (for the test sample) and G (for the standard sample) as indicated at 70. The window size, n, (which in an integer less than N) and the figure-of-merit reference value, $\zeta$, are selected by the operator, or are preselected as indicated at 72. I=1 and M=n+1 are set as indicated at 74 and Z(I,M) is evaluated by implementation of Equation 8 as indicated at 76. If Z(I,M)>$\zeta$ as indicated at 78, then the method of the present invention evaluates the test sample as containing a flaw as indicated at 80. If Z(I,M)<$\zeta$, increment I and M, i.e., I=I+1 and M=M+1 as indicated at 82 and check if M>N (if M has exceeded the number of data points) at 84. If not, calculate Z(I,M) by Equation 8 as indicated at 76. If Z(I,M)>$\zeta$ the method of the present invention evaluates the test sample TS as containing a flaw at 80. If Z(I,M) is not greater than $\zeta$, increment I and M again and repeat until either Z(I,M)>$\zeta$ or M>N. The procedure can be repeated until M>N, at which point the analysis stops as indicated at 86. All cases for which Z(I,M)>$\zeta$ are identified. Obtaining all of Z(I,M) indicates not only that a flaw is likely, when Z(I,M)>$\zeta$, but will also indicate the location of the flaw along test sample TS.

Following are some illustrative examples. A test sample scan profile was collected using a collimated source-detector arrangement as shown in FIG. 1 over a solid 1-inch wide by 4-inch tall aluminum bar (substrate SU) covered with a 0.84-mm thick aluminum sheet (cover CO). The bar had a small (¼-inch diameter by ⅛-inch deep) hole milled in it, which was filled with $Al_2O_3$ powder, simulating interface corrosion representative of a horizontal disk-shaped flaw of FIGS. 7a and 7b. FIG. 14 gives the measured values of R for 23 scan positions. The average of the first five values of R is 11,579.4 counts. One Hundred (100) pseudo-random numbers were generated from a Poisson distribution with mean 11,579; the first 23 of these values are shown in FIG. 14 in the column marked S and represent a template for a standard sample. Another set of 23 of the pseudo-random numbers are used as a second test sample scan, T, representative of an unflawed test sample.

Figure 11:
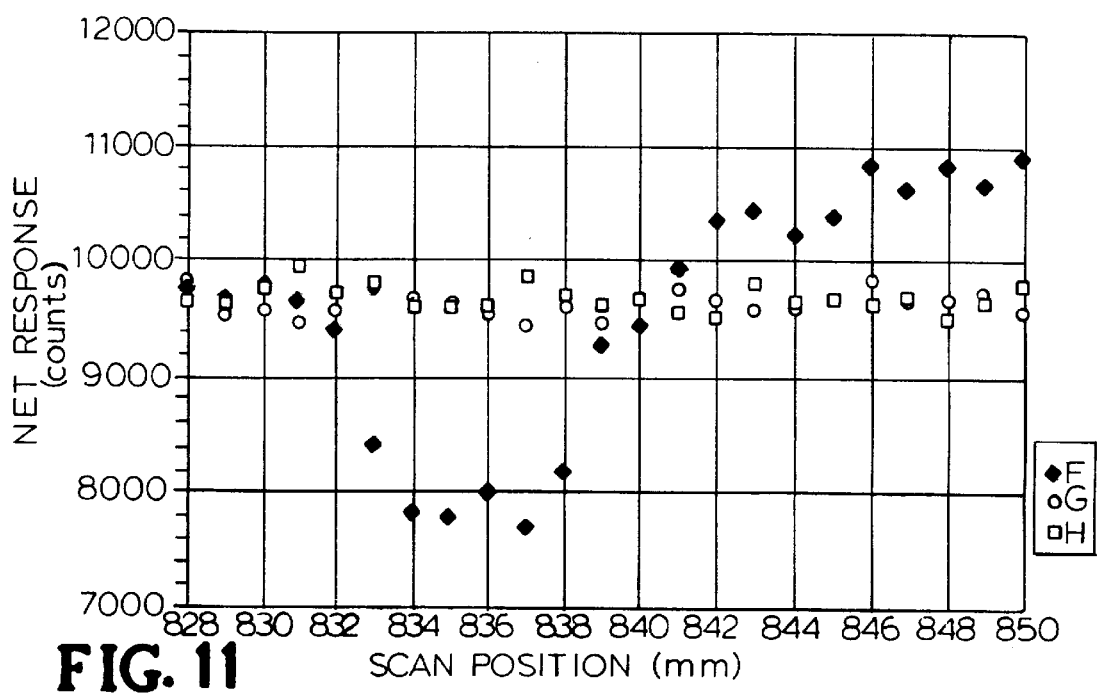
FIG. 11 is a graphical representation comparing conditioned scan profiles generated from the data contained in FIG. 14.

A constant cover-only background of C=1,895 counts are subtracted from all three scan profiles, forming the conditioned scan profiles F, G, and H. FIG. 11 plots the three scan profiles F, G, and H, with the net response in counts on the y-axis and the scan position in mm on the x-axis. It is obvious that F differs from G in FIG. 11, due to the presence of the $Al_2O_3$-filled hole in the substrate. However, the comparison of H to the template G shows no discernible difference, beyond the inherent statistical variations in counts. The values of the function Z of Equation (8) are calculated for I=1 and M=23, obtaining Z=40.33 for the test sample scan F and Z =1.22 for the test sample scan H. Application of the algorithm with $\zeta$=1.5 (or any value above 1.22) clearly differentiates the test sample scan F for the bar containing the $Al_2O_3$ "flaw" from the second flaw-free test sample response H.

Figure 12:
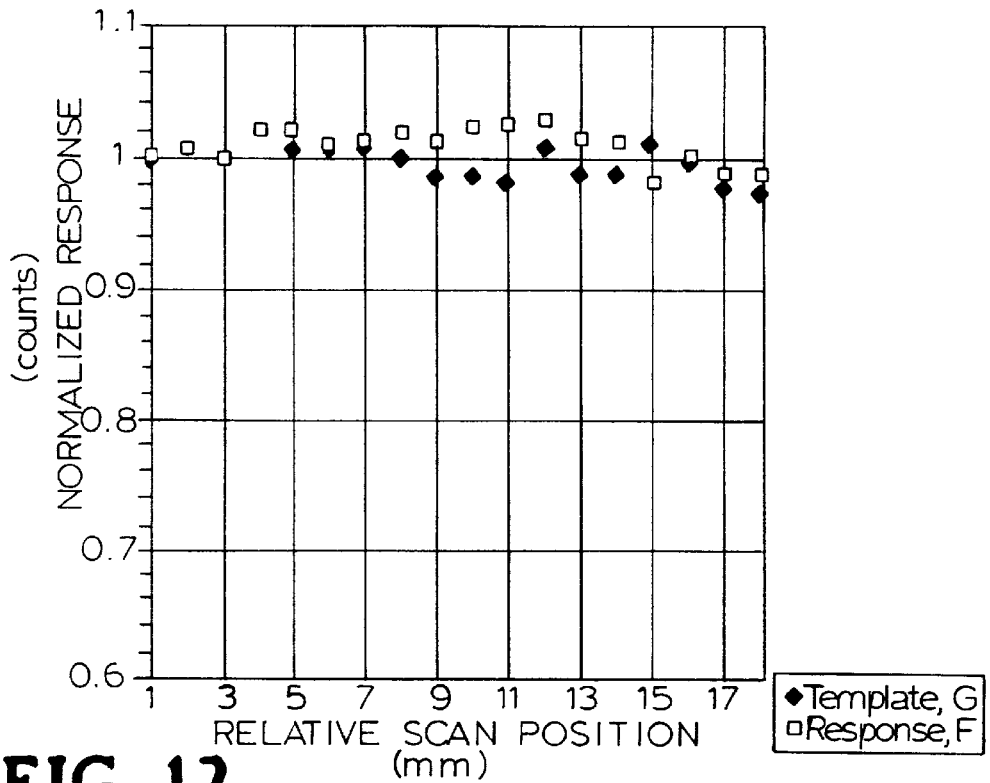
FIG. 12 is a graphical illustration of normalized responses generated from the data contained in FIG. 15.
Figure 13:
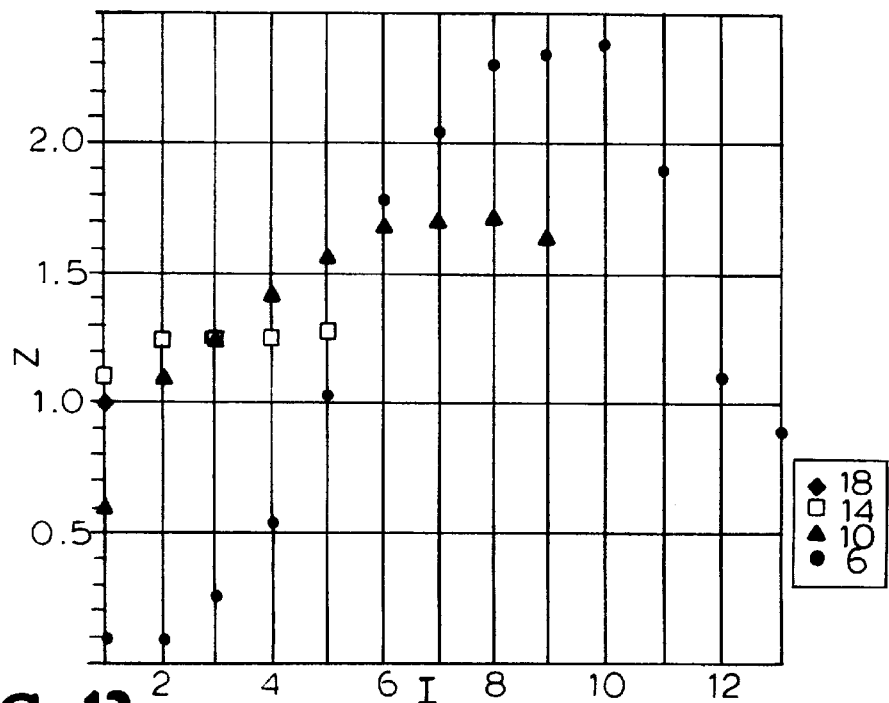
FIG. 13 is a graphical illustration of the figure-of-merit Z obtained by the rolling-window method for four values of window width (n=6, n=10, n=14, and n=18)

With continuing reference to the rolling window method of the invention, responses were measured along a rivet-line on an aircraft section in 1-mm steps over a length of 54 mm; one of the rivets had a small (½-in diameter) hole next to it on the underside substrate, the hole did not extend into the top skin layer and was not visible from the top. Eighteen of the measured scan responses were taken as the template, S, and the eighteen responses nearest the rivet with the hole were taken as the test-sample profile, R. These data are given in FIG. 15. Using the values $S_0$=9,918 and $R_0$=10,104 (obtained by averaging the first four and the last four counts in each scan) the responses were normalized by application of Equations (5a) and (6a). The normalized responses G and F are given in FIG. 15 and plotted in FIG. 12. Visual inspection of FIG. 12 does not conclusively verify that F differs significantly enough from G to indicate whether or not a flaw is present. The template-matching method of the present invention was then utilized and Z calculated for the test sample, F, for n=18, and I=1. With n=18, the value obtained, Z=0.9987, was very nearly unity. The rolling-window method was applied setting n=14, n=10, n=6, and $\zeta$=1.5. FIG. 13 shows the resulting values of Z versus I. For n=10 and n=6, Z exceeds $\zeta$=1.5 for some values of I, indicating a flaw is probably present in the test sample. Use of the rolling-window template-matching method of the present invention can isolate very small deviations of a test-sample profile from a template sample and identify approximately where the flaw is located. In fact, since for n=6, Z first exceeds $\zeta$ for scan points 6–11, is a maximum near I=10, and last exceeds 4 for scan points 11–16, it is concluded that the flaw is located near the region corresponding to I=10–11.

In summary and from the foregoing description it can be seen that the flaw detection method and apparatus of the invention provides these several advantages over heretofore known flaw detection methods and apparatus:

a) while the transmission mode can be used, it is not required as in many existing tomographic and radiographic techniques, thus larger samples can be examined.

b) relatively low intensity sources can be used which avoids the safety and maneuverability implications of the prior method of flaw detection.

c) a single-figure-merit is generated by the invention method thereby eliminating the subjective interpretation of images.

d) statistical counting uncertainties are incorporated in the method in a way that allows the user to specify the sensitivity of the flaw detection method, through specification of a single parameter, $\zeta$.

e) flaw detection is accomplished by local interrogation using source and/or detector collimation, thus reducing system-wide interferences typical of ultrasound and broad-beam radiographic methods.

f) there is no need to perform X- or γ-ray spectroscopy, which requires more sophisticated equipment than is used in the invention method and further requires high-intensity sources in order to produce enough counts within each energy bin of the measured response spectrum to minimize statistical uncertainties.

While the invention has been described with reference to specific embodiments thereof, it will be appreciated that numerous variations, modifications, and embodiments are possible, and accordingly, all such variations, modifications, and embodiments are to be regarded within the spirit and scope of the invention.

What is claimed is:

1. A method for non-destructive examination of a test sample comprising the steps of:
   a) directing radiation into said test sample;
   b) directing radiation into an unflawed standard sample;
   c) detecting radiation emanating from said test sample to obtain a set of responses R;
   d) detecting radiation emanating from said standard sample to obtain a set of responses S;
   e) utilizing said set of responses R and said set of responses S to obtain a single figure-of-merit; and
   f) determining the deviation of said single figure-of-merit from a reference value.

2. The method of claim 1, wherein said figure-of-merit is determined according to the following:

$$Z(I, M) = \sum_{i=I}^{M} \frac{[S_i - R_i]^2}{\sigma^2(S_i) + \sigma^2(R_i)}$$

wherein:
   $\sigma(S_i)$ is a measure of the uncertainty in the response $S_i$
   $\sigma(R_i)$ is a measure of the uncertainty in the response $R_i$
   $S_i$ is the $i^{th}$ response for said standard sample;
   $R_i$ is the $i^{th}$ response for said test sample;
   I is a number that identifies the first response; and
   M is a number that identifies the last response.

3. A method for non-destructive examination of a test sample comprising the steps of:
   a) directing a radiation beam into said test sample and a standard sample;
   b) scanning said radiation beam in discrete steps across said test sample and said standard sample;
   c) detecting radiation emanating from said test sample with one or more detectors to obtain a set of responses R corresponding to said discrete steps along said test sample;
   d) detecting radiation emanating from said standard sample with one or more detectors to obtain a set of responses S corresponding to said discrete steps along said standard sample;
   e) utilizing said set of responses R and said set of responses S to obtain a single figure-of-merit; and
   f) determining the deviation of said single figure-of-merit from a reference value.

4. The method of claim 3, wherein said figure-of-merit is determined according to the following:

$$Z(I, M) = \sum_{i=I}^{M} \frac{[S_i - R_i]^2}{\sigma^2(S_i) + \sigma^2(R_i)}$$

wherein:
   $\sigma(S_i)$ is a measure of the uncertainty in the response $S_i$
   $\sigma(R_i)$ is a measure of the uncertainty in the response $R_i$
   $S_i$ is the $i^{th}$ response for said standard sample at scan position i;
   $R_i$ is the $i^{th}$ response for said test sample at scan position i;
   I is the number of the first scan point; and
   M is the number of the final scan point.

5. The method of claim 3, wherein the size of each said discrete step along said test and standard samples is less than the lateral width of the detector collimator cone at the depth in the sample at which a flaw is suspected.

6. The method of claim of claim 3, further comprising the steps of employing a radiation source and detector exterior to one side of said test and standard samples, wherein said detector detects the radiation having been backscattered from said test and standard samples.

7. The method of claim 3, further comprising the steps of:
   a) determining a set of background responses obtained when no sample is present or when only a cover to said standard sample is present
   b) substracting said set of background responses from said set of responses R and said set of responses S.

8. The method of claim 3, further comprising the steps of:
   a) normalizing responses for the test sample according to the following:

$$F = \frac{R}{R_o}$$

wherein:
   R=set of responses obtained from said test sample; and
   $R_o$=normalization constant; and
   b) normalizing responses for said standard sample according to the following:

$$G = \frac{S}{S_o}$$

wherein:
   S=set of responses obtained from said standard sample; and
   $S_o$=normalization constant.

9. The method of claim 3 further comprising the steps of:
   a) determining a set of background responses, C, obtained when no sample is present or when only a cover to said standard sample is present, substracting said set of background responses from said set of responses R, and normalizing responses for said test sample according to the following:

$$F = \frac{R - C}{R_o}$$

wherein $R_o$ is a normalization constant; and
   b) subtracting said set of background responses from said set of responses S, and normalizing responses for the standard sample according to the following:

$$G = \frac{S - C}{S_o}$$

wherein $S_o$ is a normalization constant.

10. The method of claim 3 further comprising the steps of comparing n consecutive scan points, where n<the total number of scan points N, of said set of responses R to the corresponding n consecutive scan points of said set of responses S, to obtain a figure-of-merit corresponding to n.

11. The method of claim 10 further comprising the steps of repeatedly comparing n consecutive scan points of said set of responses R to the corresponding n consecutive scan points of said set of responses S, where n is defined by a first scan point, I=1,2, . . . N−n+1, and by a last scan point, M=n, n+1, . . . , N, repeating said comparisons up to a maximum of I=N−n+1.

12. A radiation apparatus for use in association with a test sample comprised of a cover overlying a substrate material to determine in a non-destructive manner whether hidden flaws exist in the test sample, said apparatus comprising:
 a) at least one radiation source for emitting X- or γ-radiation beams into said test sample;
 b) at least one detector located in spaced relationship to said radiation source for detecting radiation emanating from said sample;
 c) means for positioning said beams in discrete steps sequentially across said test sample to obtain a set of responses R, wherein the size of each said discrete step along said test and standard samples is less than the lateral width of the detector collimator cone at the depth in the sample at which a flaw is suspected
 d) means associated with said detector for storing radiation responses therefrom;
 e) means for utilizing said set of responses R from said test sample and a corresponding set of responses S from a standard sample to obtain a single figure-of-merit.

* * * * *

UNITED STATES PATENT AND TRADEMARK OFFICE
CERTIFICATE OF CORRECTION

PATENT NO. : 6,157,699
DATED : December 5, 2000
INVENTOR(S) : William L. Dunn

It is certified that error appears in the above-identified patent and that said Letters Patent are hereby corrected as shown below:

Column 1, line 62, "G-ray" should read -- $\gamma$-ray -- . (PTO error)
Column 2, line 23, "'269 patent" should read --'296 patent--. (Applicant error)
Column 2, line 26, "'269 patent" should read --'296 patent--. (Applicant error)
Column 2, line 49, "y rays" should read -- $\gamma$-rays -- . (Applicant error)
Column 3, line 32, "Leo" should read --To--. (PTO error)
Column 4, line 37, after "invention", a period should be inserted. (Applicant error)
Column 5, line 8, after "n=18", a period should be inserted. (Applicant error)
Column 5, line 52, after "Newbury", insert a comma. (Applicant error)
Column 6, line 12, "led" should read --fed--. (PTO error)
Column 8, line 20, "I-or" should read --for--. (PTO error)
Column 9, line 12, "requires" should read --require--. (Applicant error)
Column 10, line 42, after "G=S", insert a period. (PTO error)
Column 11, line 47, "p and a" should read -- $\mu$ and $\sigma$ -- . (PTO error)
Column 11, line 61, " $S_\kappa \sqrt{P_\kappa} = 4.$ " should read -- $S_\kappa = \sqrt{P_\kappa}$ . -- . (PTO error)
Column 14, line 4, "( 1/2 - in. diameter)" should read --(1/16 - in. diameter)--. (PTO error)
Column 14, line 31, "4" should read -- $\zeta$ -- . (PTO error)
Column 16, line 3, "of claim of claim 3," should read --of claim 3,-- . (Applicant error)

Signed and Sealed this

Twenty-fourth Day of April, 2001

Attest:

NICHOLAS P. GODICI

Attesting Officer

Acting Director of the United States Patent and Trademark Office